United States Patent
Koop

(10) Patent No.: US 7,094,252 B2
(45) Date of Patent: Aug. 22, 2006

(54) ENHANCED NONINVASIVE COLLAGEN REMODELING

(75) Inventor: Dale E. Koop, Roseville, CA (US)

(73) Assignee: CoolTouch Incorporated, Roseville, CA (US)

( * ) Notice: Subject to any disclaimer, the term of this patent is extended or adjusted under 35 U.S.C. 154(b) by 0 days.

(21) Appl. No.: 09/934,356

(22) Filed: Aug. 21, 2001

(65) Prior Publication Data

US 2003/0040739 A1    Feb. 27, 2003

(51) Int. Cl.
*A61N 5/06* (2006.01)
*A61N 7/00* (2006.01)
*A61B 18/18* (2006.01)

(52) U.S. Cl. .................. 607/88; 607/96; 606/9
(58) Field of Classification Search ............... 606/7–9, 606/27, 32; 607/88–91, 96–102; 128/898
See application file for complete search history.

(56) References Cited

U.S. PATENT DOCUMENTS

| | | | |
|---|---|---|---|
| 4,976,709 A | 12/1990 | Sand | |
| 5,137,530 A | 8/1992 | Sand | |
| 5,304,169 A | 4/1994 | Sand | |
| 5,374,265 A | 12/1994 | Sand | |
| 5,484,432 A | 1/1996 | Sand | |
| 5,599,788 A * | 2/1997 | Purchio et al. | 514/2 |
| 5,607,691 A * | 3/1997 | Hale et al. | 424/449 |
| 5,810,801 A | 9/1998 | Anderson et al. | |
| 5,814,040 A | 9/1998 | Nelson et al. | |
| 5,817,089 A * | 10/1998 | Tankovich et al. | 606/9 |
| 5,820,626 A | 10/1998 | Baumgardner | |
| 5,885,274 A | 3/1999 | Fullmer et al. | |
| 5,968,034 A | 10/1999 | Fullmer et al. | |
| 5,976,123 A * | 11/1999 | Baumgardner et al. | 606/13 |
| 5,983,900 A | 11/1999 | Clement et al. | |
| 6,106,514 A * | 8/2000 | O'Donnell, Jr. | 606/9 |
| 6,124,273 A | 9/2000 | Drohan et al. | |
| 6,273,885 B1 | 8/2001 | Koop et al. | |
| 6,312,450 B1 * | 11/2001 | Yavitz et al. | 607/88 |
| 6,319,274 B1 * | 11/2001 | Shadduck | 607/89 |
| 6,451,007 B1 * | 9/2002 | Koop et al. | 606/9 |
| 6,455,501 B1 * | 9/2002 | Rodgers et al. | 514/16 |
| 6,663,659 B1 * | 12/2003 | McDaniel | 607/88 |
| 2003/0119076 A1 * | 6/2003 | Ruben et al. | 435/7.21 |

FOREIGN PATENT DOCUMENTS

EP    A2 0043447    6/1981

OTHER PUBLICATIONS

Spatially selective photocoagulation of biological tissues: feasibility study utilizing cryogen spray cooling, Applied Optics; vol. 35, No. 19; Anvarie et al., Jul. 1, 1996, 9 pages.

* cited by examiner

*Primary Examiner*—A. Farah
(74) *Attorney, Agent, or Firm*—Ray K. Shahani, Esq.

(57) ABSTRACT

A method and apparatus for treatment of skin or other tissue, using a source of thermal, electromagnetic radiation, electrical current, ultrasonic, mechanical or other type of energy, to cause minimally-invasive thermally-mediated effects in skin or other tissue which stimulates a wound-healing response, in conjunction with topical agents or other wound healing compositions, for application on the skin or other tissue which accelerate collagenesis, such as in response to wound healing. The dosage and time period of application of the compositions are adjusted to prevent external or surface tissue damage.

7 Claims, 2 Drawing Sheets

ENHANCED NONINVASIVE COLLAGEN REMODELING

FIELD OF THE INVENTION

This invention is related to the controlled delivery of photothermal or other type of energy for treatment of biological or other tissue, and more specifically, a method, system and kit for causing a subdermal wound such that upon application of a growth factor, collagenesis and further repair and healing improvement of tissue is accelerated.

BACKGROUND OF THE INVENTION

Collagen is the single most abundant animal protein in mammals, accounting for up to 30% of all proteins. The collagen molecule, after being secreted by the fibroblast cell, assembles into characteristic fibers responsible for the functional integrity of tissues making up most organs in the body. The skin is the largest organ of the body occupying the greatest surface area within the human body. As age advances and as a result of other noxious stimuli, such as the increased concentration of the ultraviolet part of the electromagnetic spectrum as radiated from the sun, structural integrity and elasticity of skin diminishes.

Crosslinks between adjacent molecules are a prerequisite for this integrity of the collagen fibers to withstand the physical stresses to which they are exposed. A variety of human conditions, normal and pathological, involve the ability of tissues to repair and regenerate their collagenous framework. In the human, 13 collagen types have been identified. Of the different identifiable types, type I is the most abundant in skin where it makes up 80 to 90% of the total collagen connective tissue. This type of collagen, however, is less dynamic in the full-grown individual than its counterparts in which collagen is involved in active remodeling. In this case the normal collagen synthesizing activities in skin is relatively quiescent exhibiting slow, almost negligible, turnover.

The extra-cellular matrix of the various connective tissues, such as skin, consists of complex macromolecules, collagen, elastin and glycosaminoglycans (GAGs). The biosynthesis of these macromolecules involves several specific reactions that are often under stringent enzymatic control. The net accumulation of connective tissues is thus, dependent upon the precise balance between the synthesis and the degradation of the connective tissue components.

Previous disclosures, such as U.S. Pat. No. 4,976,799 and U.S. Pat. No. 5,137,539 have described methods and apparatus for achieving controlled shrinkage of collagen tissue. These prior inventions have applications to collagen shrinkage in many parts of the body and describe specific references to the cosmetic and therapeutic contraction of collagen connective tissue within the skin. In the early 1980's it was found that by matching appropriate laser exposure parameters with these conditions, one had a novel process for the nondestructive thermal modification of collagen connective tissue within the human body to provide beneficial changes. The first clinical application of the process was for the non-destructive modification of the radius of curvature of the cornea of the eye to correct refractive errors, such as myopia, hyperopia, astigmatism and presbyopia. New studies of this process for the previously unobtainable tightening of the tympanic membrane or ear drum for one type of deafness have been made.

In addition to addressing the traditional method of collagen shrinkage wherein the ambient temperature is elevated within the target tissue by about 23 degrees Celsius, the "thermal shrinkage temperature" of collagen, $T_s$, a novel method for obtaining controlled contraction of collagen at a much lower temperature has been developed. Evidence exists to elevate the mechanical role played by the GAGs in the collagenous matrix. Removing or altering these interstitial chemicals by enzymes or other reagents as disclosed in U.S. Pat. No. 5,304,169 considerably weakens the connective tissue integrity and influences the thermal transformation temperature $(T_s)$. Shrinkage temperature may be defined, therefore, as the specific point at which disruptive tendencies exceed the cohesive forces in this tissue. This temperature, thus, makes this an actual measurement of the stability of the collagen bearing tissue expressed in thermal units.

The cause of wrinkles around the eyelids, mouth and lips is multifactorial: photodamage, smoking and muscular activity such as squinting and smiling all contribute. The end result is a general loss of elasticity, which is a textural skin condition as opposed to a skin redundancy or excess of skin tissue. The surgical injection of reconstituted collagen is commonly used in order to flatten the perioral lines. While oculoplastic surgeons may treat this problem around the eye inappropriately by blepharoplasty, it has been observed that even transconjunctival blepharoplasty for removal of prolapsed retrobulbar fat fails to address the fine periocular lines or wrinkles. Until recently, the main approach to treating these blemishes has been chemical peeling by means of trichloroacetic acid or phenol. Complications of chemical peels may include hypopigmentation, scarring, cicatricial ectropion and incomplete removal of the wrinkles.

Many patients are acutely aware of these cosmetic blemishes as evidenced by the large quantity of money spent each year in the U.S. and abroad upon home and spa remedies for a more youthful appearance. With the advent of laser technology as an alternative to chemical peels or dermabrasion, dermal ablation techniques with both the conventional carbon dioxide lasers and the high energy, short duration pulse waveform CO2 lasers, high tech solutions appear to provide substantial benefits to patients.

CO2 laser resurfacing is not a new technique. CO2 lasers have been used for several years, but regular continuous wave CO2 lasers can cause scarring due to the tissue destruction caused as heat as conducted to adjacent tissue. Even superpulse CO2 lasers produce excessive thermal damage. The Ultrapulse CO2 laser introduced by Coherent, Inc. is an attempt to assuage these drawbacks by offering a high energy, short duration pulse waveform limiting the damage to less than 50 microns allowing a char-free, layer by layer vaporization of the skin tissue.

All of the foregoing procedures depend for their success upon primary damage and the reparative potential induced by the inflammatory process in the tissue. Associated with inflammation are, of course, the four cardinal signs of inflammation of rubor (hyperemia), calor (thermal response), dolor (pain), and tumor or edema or swelling. Coincident with these manifestations is the risk of reduced resistance to infection. One must not forget that these collateral effects accompany a cosmetic enhancement procedure and, for the most part, are not associated with a therapeutic procedure. Therefore, the development of a more efficacious method would be beneficial in this regard.

Various undesirable skin conditions would be improved if the collagen underlying the region of the condition could safely be improved without damage to the overlying region. Wrinkles related to photodamage and acne scars are example of such conditions.

U.S. Pat. Nos. 4,976,709, 5,137,530, 5,304,169, 5,374,265, 5,484,432 issued to Sand, disclose a method and apparatus for controlled thermal shrinkage of collagen fibers in the cornea using light at wavelengths between 1.8 and 2.55 microns. However strong absorption of the laser energy by water limits the penetration depth to the most superficial layers of skin.

The CoolTouch (trademark) 130 laser system by Cool-Touch Corp of Auburn, Calif., was first introduced at the Beverly Hills Eyelid Symposium in 1995. It utilizes a laser at a wavelength of 1.32 microns to cause thermally mediated skin treatment. In this device the treatment energy is targeted at the surface of the skin with in depth optical heating of the epidermis, papillary dermis, and upper reticular dermis. The energy is primarily absorbed in tissue water with a skin absorption coefficient of 1.4 cm−1, corresponding to an absorption depth of 0.71 cm. Scattering of the 1.32 micron wavelength light by skin microstructures alters the distribution of light from an exponential attenuation to a more complex distribution, which has much faster attenuation approximating an absorption depth of 0.1 cm. Most of the energy is absorbed in the first 250 microns of tissue. To prevent overheating of the epidermis pulsed cryogen spray precooling is used. U.S. Pat. No. 5,814,040, issued Sep. 29, 1998, describes a dynamic cooling method utilizing pulsed cryogen spray precooling. Skin treated with this device has improved texture and a reduction in wrinkles and scarring due to the long term renewal of dermal collagen without significant skin surface wounding.

U.S. Pat. No. 5,810,801 teaches a method and apparatus for treating a wrinkle in skin by targeting tissue at a level between 100 microns and 1.2 millimeters below the surface, to thermally injure collagen without erythema, by using light at wavelengths between 1.3 and 1.8 microns. The parameters of the invention are such that the radiation is maximally absorbed in the targeted region. The invention offers a detailed description of targeting the 100 micron to 1.2 mm region by utilization of a lens to focus the treatment energy to a depth of 750 microns below the surface. Because of the high scattering and absorption coefficients, precooling is utilized to prevent excess heat build up in the epidermis when targeting the region of 100 microns to 1.2 mm below the surface. The wavelength range of use is 1.3 microns to 1.8 microns in order to avoid the wavelength range of Sand. However the wavelength range of 1.4 to 1.54 microns and the range between 2.06 and 2.2 microns have identical effective attenuation coefficients in skin. Also the range from 1.15 to 1.32 microns has a fairly uniform effective attenuation coefficient in skin of about 6 to 7 cm−1. The effective attenuation length in skin for the range of wavelengths of 1.3 to 1.8 microns varies from 6 cm−1 at 1.3 microns to 52 cm−1 microns, corresponding penetration depths in skin of 200 microns to 2 millimeters. Specific laser and cooling parameters are selected so as to avoid erythema and achieve improvement in wrinkles as the long term result of a new collagen formation following treatment.

Kelly et al, report improvement in skin due to collagen remodeling after treatments with an Nd:YAG laser at 1.32 microns and cryogen spray precooling. In this case the method was designed to provide a series of treatments with parameters selected to produce erythema and mild edema, with some improvement in facial rhytids several months following a series of treatments. However, there is a risk of pigmentary change or transient pitted scarring because of the high fluence level of the laser, greater than 30 joules per square centimeter in 20 millisecond exposures, and the high level of pulse cryogen cooling.

Mucini et al. reported effective dermal remodeling using a 980 nm diode laser with a spherical handpiece which focused irradiation into the dermis avoiding the high scattering and absorption characteristic of longer wavelengths. The device requires a small lens of a few millimeters in contact with skin and results in a slow procedure when used for facial areas.

Ross et al., reported the use of an Erbium:YAG laser operating at a wavelength of 1.54 microns fired in a multiple pulsed mode has been described for eliciting changes in photodamaged skin. A chilled lens in contact with skin at the treatment site was used in an attempt to spare the epidermis. Treatment occurred during a period of several seconds with a sequence of cooling and heating with the laser and handpiece. At 1.54 microns the optical penetration depth 0.55 mm and the authors reported that the surface must be chilled before the laser exposure requiring a complex method of cooling and laser exposure. The authors state that a more superficial thermal injury may be needed than could be achieved, and that there are increased patient risks because it would demand more accurate and precise control of heating and cooling.

Bjerring et al, reported the use of a visible light laser, operating at 585 nm wavelength, to initiate collagenesis following interaction of laser energy with small blood vessels in skin.

Other methods of creating subepidermal wounding may utilize electrical current, ultrasonic energy or non-coherent light sources. In all of these methods, including those using lasers, collagen remodeling is a long-term minimal response to the application of energy. Since the objective is a non-invasive or minimally invasive procedure the stimulation of collagenesis must be below the threshold for creating an open wound, resulting in a minimal treatment.

U.S. Pat. No. 5,599,788 describes a method of producing recombinant transforming growth factor .beta.-induced H3 protein and the use of this protein to accelerate wound healing. The protein is applied directly to a wound or is used to promote adhesion and spreading of dermal fibroblasts to a solid support such as a nylon mesh which is then applied to the wound.

It is heretofore unknown to combine the adverse effect caused by excessive photothermal, mechanical or other type of energy applied to skin or other tissue coupled with a topical or other administration of growth factor(s) or wound healing factor(s) in order to amplify the natural stimulation of growth or collagenesis caused by the wound.

OBJECTS AND ADVANTAGES OF THE PRESENT INVENTION

The object of this invention is to provide a method and device for improving skin by treating layers of skin without damaging the surface or deep skin layers. It is another object of this invention to provide a method and device for improving acne scars or photodamaged skin without causing a surface injury to skin. It is another object of this invention to provide a method and device for accelerating the collagenesis after treating skin without damaging the surface of skin.

It is yet a further advantage and object of the present invention to combine the adverse effect caused by excessive photothermal, mechanical or other type of energy applied to skin or other tissue coupled with a topical or other administration of growth factor(s) or wound healing factor(s) in order to amplify the natural stimulation of growth or collagenesis caused by the wound.

The present invention circumvents the problems of the prior art and provides a system for achieving erythema and mild edema in an upper layer of skin without the risk of high fluence levels or surface wounds. The invention offer advantages over existing devices by allowing the use of lower fluence levels resulting in faster treatments and less cost. Collagen remodeling is induced by distributing the therapeutic energy over a series of more benign treatments spaced weeks apart. The collagen remodeling is further enhanced by the use of a transforming growth factor which accelerates the wound healing response. Th growth factor is applied topically in a media which will act on the skin.

Numerous other advantages and features of the present invention will become readily apparent from the following detailed description of the invention and the embodiments thereof, from the claims and from the accompanying drawings.

SUMMARY OF THE PRESENT INVENTION

The present invention is a method and apparatus for skin or other tissue treatment, using a source of thermal energy, which may be electromagnetic radiation, electrical current, or ultrasonic energy, to cause minimal-invasive thermally-mediated effects in skin or other tissue leading to a wound-healing response, in conjunction with topical agents which accelerate collagenesis in response to wound healing. The dosage and time period of application are adjusted to prevent external or surface tissue damage.

DETAILED DESCRIPTION OF THE PREFERRED EMBODIMENT

Figure 1:
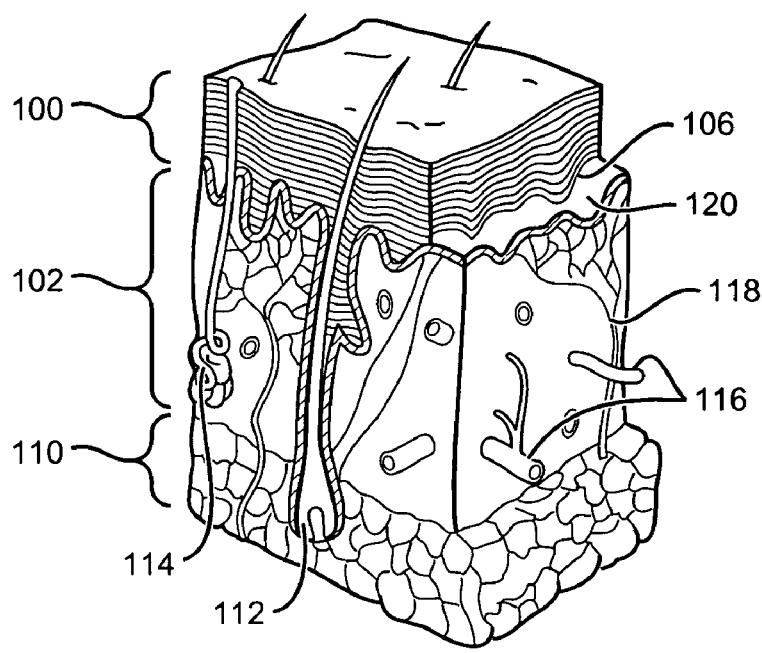
FIG. 1 is a cross-section view of typical skin tissue.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function may have like reference numerals associated therewith.

Definitions

An "absorption coefficient" of a substance is a measure of the fraction of incident light that is absorbed when light is passed through the substance. The absorption coefficient (typically in units of $cm^{-1}$) varies with the nature of the absorbing substance and with the wavelength of the light.

"Collagen" as used herein refers to any of the several types of collagen.

Collagen biosynthesis is said to be "inhibited' when cells treated with the claimed methods secrete collagen at a rate that is less than about 70% of that of untreated cells. Preferably, treated cells secrete collagen at a rate that is less than about 50%, and more preferably less than about 30% of the rate at which untreated cells secrete collagen.

Collagen biosynthesis is said to be 'stimulated' when cells treated with the claimed methods secrete collagen at a rate that is greater than about 110% of the rate at which untreated cells synthesize collagen. Preferably, treated cells secrete collagen at a rate that is about 150%, and more preferably greater than about 200% greater than that of untreated cells.

"Monochromatic" light is of one wavelength or a narrow range of wavelengths. If the wavelength is in the visible range, monochromatic light will be of a single color. As used herein, "monochromatic" refers to light that has a bandwidth of less than about 100 nm. More preferably, the bandwidth will be less than about 10 nm, and most preferably less than about 1 nm.

"Non-coherent light energy" is light that is non-laser. Unlike laser light, which is characterized by having its photon wave motions in phase, the wave motions of the photons that make up non-coherent light are in a randomly occurring phase order or are otherwise out of phase.

A "wound" as used herein, refers to any damage to any tissue in a living organism. The tissue may be an internal tissue, such as the stomach lining or a bone, or an external tissue, such as the skin. As such, a wound may include, but is not limited to, a gastrointestinal tract ulcer, a broken bone, a neoplasia, and cut or abraded skin. A wound may be in a soft tissue, such as the spleen, or in a hard tissue, such as bone. The wound may have been caused by any agent, including traumatic injury, infection or surgical intervention.

A "growth factor" as used herein, includes any soluble factor that regulates or mediates cell proliferation, cell differentiation, tissue regeneration, cell attraction, wound repair and/or any developmental or proliferative process. The growth factor may be produced by any appropriate means including extraction from natural sources, production through synthetic chemistry, production through the use of recombinant DNA techniques and any other techniques, including virally inactivated, growth factor(s)-rich platelet releasate, which are known to those of skill in the art. The term growth factor is meant to include any precursors, mutants, derivatives, or other forms thereof which possess similar biological activity(ies), or a subset thereof, to those of the growth factor from which it is derived or otherwise related.

FIG. 1 is a cross-section view of typical skin tissue. The uppermost layer 98 of typical skin tissue is composed of dead cells which form a tough, horny protective coating. A thin outer layer, the epidermis 100 and a thicker inner layer, the dermis 102. Intertwining S-like finger shaped portions 104 are at the interface between the epidermal papillary layer 106 and the dermal papillary layer 108, and extend downward. Beneath the dermis is the subcutaneous tissue 110, which often contains a significant amount of fat. It is the dermis layer which contains the major part of the connective collagen which is to be shrunk, in a preferred embodiment at an approximate target depth of between about 100 and 300 microns, according to the method of the present invention, though viable collagen connective tissue also exists to a certain degree in the lower subcutaneous layer as well. Other structures found in typical skin include hair and an associated follicle 112, sweat or sebaceous glands and associated pores 114, blood vessels 116 and nerves 118. Additionally, a pigment layer 120 might be present. It will be understood that the drawing is representative of typical skin and that the collagen matrix will take different forms in different parts of the body. For example, in the eyelids and cheeks the dermis and subcutaneous layers are significantly thinner with less fat than in other areas. The target depth will be a function of the amount of scattering in the particular skin type and the associated absorption coefficient of the tissue. Furthermore, in some cases the actual target depth will correspond to one half the thickness of the subject tissue. For example, the target depth of tissue ½ inch thick might be about ¼ inch below the surface of the skin.

A. Damage to Tissue

Optimum Wavelength: 1.3–1.4 Microns

Methods and devices for modulating collagen biosynthesis are provided. The methods involve focusing non-coherent light energy of a predetermined wavelength to a target site where collagen biosynthesis can potentially occur. Depending upon the particular wavelength employed, collagen biosynthesis is either inhibited or stimulated. Generally, wavelengths in the red and near-infrared portion of the electromagnetic spectrum stimulate collagen biosynthesis, while longer wavelengths inhibit collagen biosynthesis.

In a preferred embodiment, to inhibit collagen biosynthesis, light energy of a wavelength greater than about 1.0 μm, preferably about 1.06 μm, is delivered to the target site for a time period sufficient to accomplish the inhibition. In a preferred embodiment, stimulation of collagen biosynthesis occurs when light energy at 640 nm or 900 nm is delivered to a target site for a time period sufficient to accomplish the stimulation.

The optimal wavelength within these ranges is influenced by whether the light energy must pass through overlying tissue before reaching the target site. In such cases where the target site is shielded by other tissue, the light energy is transmitted through the shielding tissue and focused on the target site so that the desired energy level is obtained at the target site. Because transmission of light through tissue is highly wavelength specific, one should choose a wavelength that is not highly absorbed by overlying tissue.

To modulate collagen biosynthesis, an amount of light energy of an appropriate predetermined wavelength is delivered to the target site that is sufficient to have the desired stimulatory or inhibitory effect. The amount of energy delivered to a target site is a function of several factors, including the output of the light source, the energy flux at the target site as determined by the source output and the degree of focusing achieved by the light delivery apparatus, and the time period for which the target site is exposed to the light energy. Another factor, discussed below, is the nature of any tissue overlying the target site.

The appropriate combinations of energy flux and time period for a desired effect on collagen biosynthesis can be determined empirically. For example, one can determine the effect on collagen biosynthesis of irradiating cells growing in tissue, preferably in monolayers, with light energy of a given wavelength, energy flux, and time period.

In general, the desired energy density delivered to the target site is between about $1.0 \times 10^3$ and $1.6 \times 10^3$ Joules $cm^{-2}$. Preferably, the energy density at the target site is about $1.1 \times 10^3$ Joules $cm^{-2}$. For most applications, the amount of energy delivered to the target site should be sufficient to modulate collagen biosynthesis, but should not be so great as to cause a significant decrease in cell proliferation. For example, $1.7 \times 10^3$ Joules $cm^{-2}$ of 1064 nm laser light is known to inhibit fibroblast proliferation. Thus, an energy that is between about $1.1 \times 10^3$ and about $1.7 \times 10^3$ Joules $cm^{-2}$ is preferred.

To achieve the desired energy density, the light energy is delivered to the target site for a sufficient time period. The time period necessary depends on the energy flux delivered to the target site by the light delivery apparatus. The light can be delivered as a single pulse or as a multiplicity of pulses. Often, the use of short pulses is preferred, as the shorter pulses cause less undesirable heating of the tissues surrounding the target site than does a single pulse of longer duration. Preferably, a higher-power shorter-duration pulse is used, rather than a low-power long-duration pulse. Typical pulse durations are between about 0.01 and 1.0 seconds, most preferably about 0.1 seconds.

Light Delivery Apparatus

Many types of non-laser light sources are suitable for producing the noncoherent light that is used in the methods and apparatus of the present invention. For example, one can employ polychromatic light sources such as heated lamp filaments or gas filled vacuum tubes. Commercially available light sources are discussed in, for example, LaRocca, A., "Artificial Sources," In *Handbook of Optics*, Vol. 1, Ch. 10, Bass et al., eds., McGraw-Hill, New York, 1995, pp. 10.3–10.50, and references cited therein.

If a polychromatic light source is used, the light energy is preferably made monochromatic or nearly monochromatic by suitable methods known to those of skill in the art. For example, one can direct the polychromatic light through a filter or a series of filters that transmits only light of the desired wavelength or range of wavelengths. Suitable filters are described in, for example, Dobrowolski, J. A., "Optical Properties of Films and Coatings," In *Handbook of Optics*, Vol. 1, Ch. 42, Bass et al., eds., McGraw-Hill, New York, 1995, pp. 42.342.130, and references cited therein. Bandpass filters are reviewed, for example, in Macleod, H. A., 7hin *film Optical E71ters*, McGraw-Hill, New York, 1986; 'Metal-dielectric Interference Filters," in *Physics of 7hin Films*, Hass et al., eds., Academic Press, New York, 1977, vol. 9, pp. 73–144; Barr, "The Design and Construction of Evaporated Multilayer Filters for Use in Solar Radiation Technology," in *Advances in Geophysics*, Drummond, ed., Academic Press, New York, 1970, pp. 391–412).

In a preferred embodiment, a monochromatic or nearly monochromatic light source is used. By choosing a light source that emits monochromatic or nearly monochromatic light, the need to filter or focus the light to the desired wavelength is eliminated. Several types of monochromatic or nearly monochromatic light source are known to those of skill in the art. See, e.g., LaRocca, supra., for types and sources of monochromatic light sources.

Light-emitting diodes (LEDs) are a preferred light source for use in the claimed invention. LEDs are described, for example, in Haitz et al., "Light-Emitting Diodes," In *Handbook of Optics*, Vol. 1, Ch. 12, Bass, M., ed., McGraw-Hill, New York, pp. 12.1–12.39. Both surface and edge emitters are commercially available, in continuous and pulse-operated modes. Commercially available LEDs that are useful in the claimed methods emit wavelengths of 830, 904, 1060, 1300, and 1550 nm. In preferred embodiments of the present invention, the 830 and 904 nm LEDs are useful for stimulating collagen biosynthesis, while in other preferred embodiments of the present invention, the 1060, 1300, and 1550 nm LEDs are appropriate for inhibition.

Light energy used in the claimed methods is preferably collimated, in addition to being of a predetermined wavelength or range of wavelengths. Collimation can be achieved by any of several methods known to those of skill in the art. For example, passing light through fiber optics of various core diameters will achieve collimation. Suitable fiber optic instrumentation is available from EG&G Opto-Electronics of Salem, Mass. Optical fibers are described, for example, in Brown, T. G., "Optical Fibers and Fiber-Optic Communications," In Handbook of Optics, Vol. U, Ch. 10, Bass, M., ed., McGraw-Hill, New York, pp. 10.1 et seq.

The light energy is focused to the target site as a spot having a diameter that is appropriate for the particular treatment being undertaken. Where inhibition of collagen biosynthesis in a relatively small area is used, the light is focused to a correspondingly small spot at the target site. Typically, the light energy is focused to a spot with a diameter in the range of about 0.25 to about 2.0 millimeters. The focusing step also concentrates the light to an energy flux that is sufficient to achieve the desired inhibition when delivered to the target site for an appropriate period of time.

Methods for focusing light to achieve a desired energy flux and spot diameter are known to those of skill in the art. For example, a focusing lens made of glass, silica, or refractory material such as diamond or sapphire is commonly employed. In a preferred embodiment, the focusing lens directs the non-coherent light energy to an optical fiber of an appropriate core diameter and composition. For example, a 100 μm diameter low-OH silica optic fiber is appropriate. A fiber that produces a relatively low amount of transmission loss is preferred, preferably less than about 15% loss over a length of up to ten meters. The fiber is typically mounted in a shaft for delivery of the non-coherent light energy to the tissue. The output end of the shaft is preferably fitted with an output tip that can dir maintaining the delivery end of the fiber a desired distance away from the tissue. This distance can be varied by substituting a longer or shorter output tip, or by slidably adjusting the position of the output tip on the shaft.

For some applications, it is desirable to use an output tip that directs the noncoherent focused light out of its side, rather than through the end of the fiber. Means for accomplishing this are known to those of skill in the art. For example, U.S. Pat. No. 5,129,895 describes the use of a reflecting surface at the end of the fiber combined with lens action on the fiber side.

The invention also provides an apparatus for modulating collagen biosynthesis according to the methods described herein. The apparatus comprises a source of noncoherent light energy, a means for collimating the light energy generated by the light source, and a means for focusing the collimated light energy to a target site. The apparatus delivers sufficient light energy to the target site to modulate collagen biosynthesis.

Therapeutic Applications

The claimed methods for modulating collagen biosynthesis are useful in treating many conditions. Depending upon the condition being treated, either inhibition or stimulation of collagen biosynthesis may be desired.

The invention also provides methods for stimulating collagen biosynthesis. These methods are also useful in the clinical setting. For example, stimulation of collagen biosynthesis is often desirable in the early stages of wound healing. The procedures employed are similar to those used for inhibiting collagen biosynthesis, except for the wavelength of light delivered to the target site. To stimulate collagen biosynthesis, one delivers light in the red or near-infrared range of the electromagnetic spectrum to the target site. For example, light energy at 640 nm or 900 nm stimulates collagen biosynthesis when delivered to a target site at specific energy densities and durations.

To enhance wound healing, collimated fight energy of an appropriate wavelength is delivered to the wound at an energy density sufficient to stimulate collagen biosynthesis. The light energy can be delivered as a single pulse, or more preferably, as a series of short pulses. The use of short pulses reduces the likelihood of undesired heating of the tissue. Preferably, the light energy delivered is sufficient to stimulate collagen biosynthesis, but is insufficient to inhibit cell proliferation.

Figure 2:
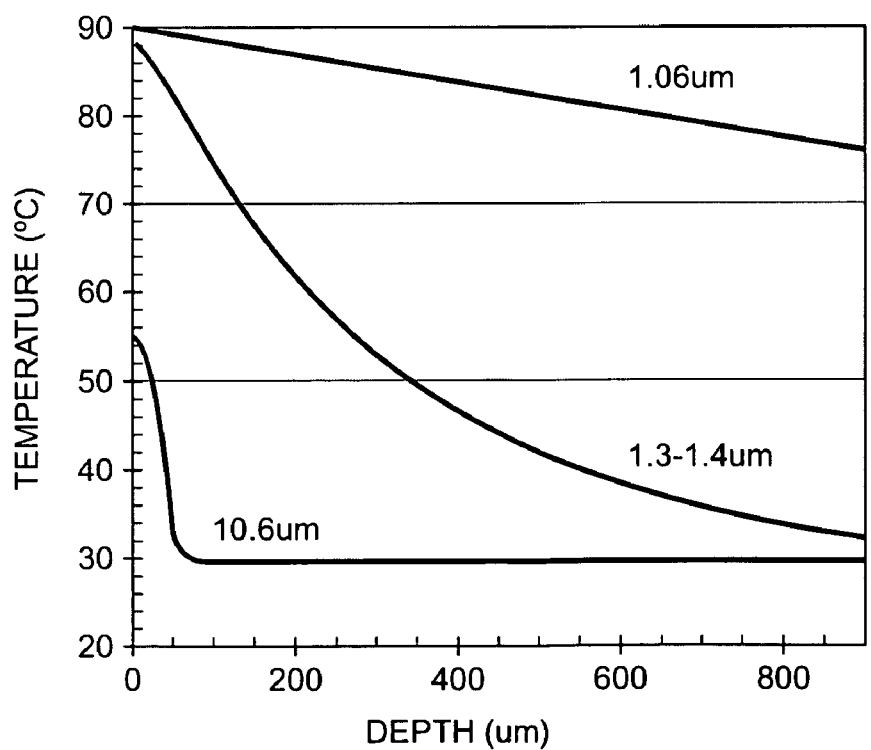
FIG. 2 is a graph demonstrating the temperature gradient through a portion of the skin as a function of both the wavelength of incident laser energy and the depth of laser radiation penetration.

FIG. 2 is a graph demonstrating the temperature gradient through a portion of the skin as a function of both the wavelength of incident laser energy and the depth of laser radiation penetration. No external cooling is used. The graph demonstrates a change in temperature ($\Delta T$) of about 60 degrees Celsius and all curves are shown for the time point 1 millisecond following exposure to the laser energy. The graph shows three lines corresponding to laser wavelengths of 10.6 microns, 1.3–1.4 microns and 1.06 microns.

The present invention utilizes laser energy having a wavelength between about 1 and about 12 microns, more preferably between about 1.2 and about 1.8 microns, and more preferably about 1.3–1.4 microns. This type of laser energy is most frequently produced by a Nd:YAG, Nd:YAP or Nd:YALO-type laser. A laser operating at these wavelengths may either have a high repetition pulse rate or operate in a continuous wave mode. This laser has been investigated in the medical community as a general surgical and tissue welding device, but has not been used for collagen tissue shrinkage in the past. Indeed, the prior art teaches away from the use of laser energy at 1.3–1.4 microns for shrinking human collagen.

The Nd:YAG, Nd:YAP and Nd:YALO-type lasers are sources of coherent energy. This wavelength of 1.3–1.4 microns is absorbed relatively well by water, and as a result is attractive for tissue interaction. It is also easily transmitted through a fiber optic delivery system as opposed to the rigid articulated arm required for the $CO_2$ laser. Very precise methods of controlling laser systems and optically filtering produced light currently exist. By selecting the appropriate combination of resonance optics and/or antireflection coatings, wavelengths in the range of 1.3–1.4 microns and even 1.32–1.34 microns can be produced.

Figure 3:
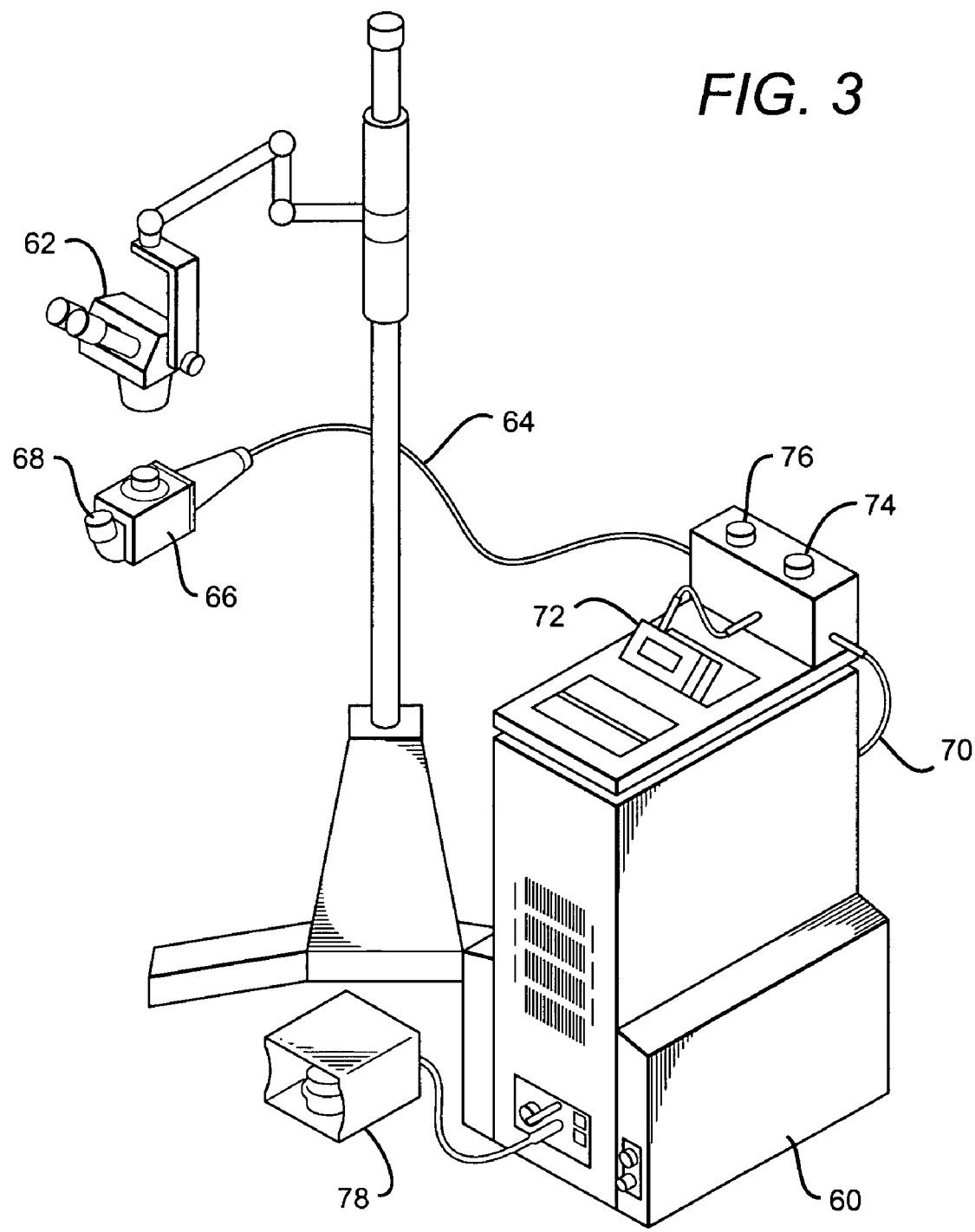
FIG. 3 is a schematic view of a microscope mounted scanner for a temperature controlled collagen shrinkage device used in the present invention.

FIG. 3 is a schematic view of a microscope mounted scanner for a temperature controlled collagen shrinkage device used in the present invention. In this view, a laser console 60 is installed adjacent a floor-mounted microscope 62. A fiber optic cable 64 conducts laser energy from the laser source to the scanner 66. A laser delivery attachment 68 may be necessary to conduct the laser energy in an appropriate beam pattern and focus. In this embodiment of the invention, servo feedback 70 signals are also conducted along the fiber optic back to the laser console. The servo feedback signals could also be directed back to the laser console via an additional fiber optic or other wiring or cabling. This servo feedback may comprise thermal or optical data obtained via external sensors or via internal systems, such as a fiber-tip protection system which attenuates the laser energy transmitted, to provide control in operation and to prevent thermal runaway in the laser delivery device. Thus, a thermal feedback controller 72 will regulate the laser energy being transmitted. This controller can comprise an analog or digital PI, PD or PID-type controller, a microprocessor and set of operating instructions, or any other controller known to those skilled in the art. Other preferred embodiments can also be provided with additional features. For example, the surgeon or technician operating the laser could also manipulate an energy adjust knob 74, a calibration knob 76 and a footpedal 78. Thus, in a preferred embodiment, a very accurately adjustable system is provided which allows a surgeon to deliver laser energy via a computer controlled scanning device, according to instructions given by the surgeon or an observer inspecting the region of the skin where collagen is to be shrunk through a very accurate microscope. Once a region to be treated is located, the scanner can deliver a very precise, predetermined amount of laser energy, in precisely chosen, predetermined regions of the skin over specific, predetermined periods of time.

In a preferred embodiment, the invention utilizes an Nd:YAG laser at 1320 nm wavelength, (such as the Cool-Touch 130, CoolTouch Corp., Auburn, Calif.) as the source of treatment energy. At 1320 nm the absorption depth in tissue is such that energy is deposited throughout the upper dermis, with most absorption in the epidermis and upper dermis, a region including the top 200 to 400 microns of tissue. The energy falls off approximately exponentially with the highest level of absorbed energy in the epidermis. Optical heating of skin follows exposure to the laser energy. If the time of exposure to the laser is very short compared to the time required for heat to diffuse out of the area exposed, the thermal relaxation time, than the temperature rise at any depth in the exposed tissue will be proportional to the energy absorbed at that depth. However, if the pulse width is comparable or longer to the thermal relaxation time of the exposed tissue than profile of temperature rise will not be as steep. Conduction of thermal energy occurs at a rate proportional to the temperature gradient in the exposed tissue. Lengthening the exposure time will reduce the maximum temperature rise in exposed tissue.

For example at 1.3 microns the laser pulse width may be set to 30 milliseconds and fluence to less than 30 joules per square centimeter. This prevents excessive heat build up in the epidermis, which is approximately the top 100 microns in skin. The papillary dermis can then be heated to a therapeutic level without damage to the epidermis. The epidermis will reach a temperature higher than but close to that of the papillary dermis.

The epidermis is more resilient in handling extremes of temperature than most other tissue in the human body. It is therefore possible to treat the papillary dermis in conjunction with the epidermis without scarring or blistering, by treating both layers with laser energy and allowing a long enough exposure time such that the thermal gradient between the epidermis and underlying layers remains low. In this way the underlying layers can be treated without thermal damage to the epidermis.

A wavelength of 1.3 microns is used in this embodiment to treat the middle layers of skin. Other wavelengths such as 1.45 or 2.1 microns may by used to treat more superficial layers of skin by this method. Visible light lasers, intense pulsed light sources, energy delivery devices such as electrical generators, ultrasonic transducers, and microdermabrasion devices may also be used to initiate a wound healing response without significant surface wounding. The use of growth factors in conjunction with these devices allows for more superficial treatments and improved response.

In one embodiment the invention utilizes an Nd:YAG laser at 1320 nm wavelength, (such as the CoolTouch 130, CoolTouch Corp., Auburn Calif.) as the source of treatment energy. At 1320 nm the absorption depth in tissue is such that energy is deposited throughout the upper dermis, with most absorption in the epidermis and upper dermis, a region including the top 200 to 400 microns of tissue. The energy falls off approximately exponentially with the highest level of absorbed energy in the epidermis. Optical heating of skin follows exposure to the laser energy. If the time of exposure to the laser is very short compared to the time required for heat to diffuse out of the area exposed, the thermal relaxation time, than the temperature rise at any depth in the exposed tissue will be proportional to the energy absorbed at that depth. However, if the pulse width is comparable or longer to the thermal relaxation time of the exposed tissue than profile of temperature rise will not be as steep. Conduction of thermal energy occurs at a rate proportional to the temperature gradient in the exposed tissue. Lengthening the exposure time will reduce the maximum temperature rise in exposed tissue.

The present invention also incorporates herein by specific reference, in their entireties, the following issued U.S. patents:

U.S. Pat. No. 5,885,274 issued Mar. 3, 1999 titled FLASH LAMP FOR DERMATOLOGICAL TREATMENT, U.S. Pat. No. 5,968,034 issued Oct. 19, 1999 titled PULSED FILAMENT LAMP FOR DERMATOLOGICAL TREATMENT, U.S. Pat. No. 5,820,626 issued Oct. 13, 1998 titled COOLING LASER HANDPIECE WITH REFILLABLE COOLANT RESERVOIR, U.S. Pat. No. 5,976,123 issued Nov. 2, 1999 titled HEART STABILIZATION, U.S. Pat. No. 6,273,885 issued Aug. 14, 2001 titled HANDHELD PHOTOEPILATION DEVICE AND METHOD.

The present invention also incorporates herein by specific reference, in their entireties, the following pending U.S. patent applications: application Ser. No. 09/185,490 filed Nov. 3, 1998 titled SUBSURFACE HEATING OF TISSUE, application Ser. No. 09/364,275 filed Jul. 29, 1999 titled THERMAL QUENCHING OF TISSUE.

B. Wound Healing and Growth Factors

When a tissue is injured, polypeptide growth factors, which exhibit an array of biological activities, are released into the wound where they play a crucial role in healing (see, e.g., Hormonal Proteins and Peptides (Li, C. H., ed.) Volume 7, Academic Press, Inc., New York, N.Y. pp. 231–277 (1979) and Brunt et al., Biotechnology 6:25–30 (1988)). These activities include recruiting cells, such as leukocytes and fibroblasts, into the injured area, and inducing cell proliferation and differentiation. Growth factors that may participate in wound healing include, but are not limited to: platelet-derived growth factors (PDGFs); insulin-binding growth factor-1 (IGF-1); insulin-binding growth factor-2 (IGF-2); epidermal growth factor (EGF); transforming growth factor-.alpha. (TGF-.alpha.); transforming growth factor-.beta. (TGF-.beta.); platelet factor 4 (PF-4); and heparin binding growth factors one and two (HBGF-1 and HBGF-2, respectively).

PDGFs are stored in the alpha granules of circulating platelets and are released at wound sites during blood clotting (see, e.g., Lynch et al., J. Clin. Invest. 84:640–646 (1989)). PDGFs include: PDGF; platelet derived angiogenesis factor (PDAF); TGF-.beta.; and PF4, which is a chemoattractant for neutrophils (Knighton et al., in Growth Factors and Other Aspects of Wound Healing: Biological and Clinical Implications, Alan R. Liss, Inc., New York, N.Y., pp. 319–329 (1988)). PDGF is a mitogen, chemoattractant and a stimulator of protein synthesis in cells of mesenchymal origin, including fibroblasts and smooth muscle cells. PDGF is also a nonmitogenic chemoattractant for endothelial cells (see, for example, Adelmann-Grill et al., Eur. J. Cell Biol. 51:322–326 (1990)).

IGF-1 acts in combination with PDGF to promote mitogenesis and protein synthesis in mesenchymal cells in culture. Application of either PDGF or IGF-1 alone to skin wounds does not enhance healing, but application of both factors together appears to promote connective tissue and epithelial tissue growth (Lynch et al., Proc. Natl. Acad. Sci. 76:1279–1283 (1987)).

TGF-.beta. is a chemoattractant for macrophages and monocytes. Depending upon the presence or absence of other growth factors, TGF-.beta. may stimulate or inhibit the growth of many cell types.

Other growth factors, such as EGF, TGF-.alpha., the HBGFs and osteogenin are also important in wound healing. Topical application of EGF accelerates the rate of healing of partial thickness wounds in humans (Schultz et al., Science 235:350–352 (1987)). Osteogenin, which has been purified from demineralized bone, appears to promote bone growth (see, e.g., Luyten et al., J. Biol. Chem. 264:13377 (1989)). In addition, platelet-derived wound healing formula, a platelet extract which is in the form of a salve or ointment for topical application, has been described (see, e.g., Knighton et al., Ann. Surg. 204:322–330 (1986)).

The heparin binding growth factors (HBGFs), including the fibroblast growth factors (FGFs), which include acidic HBGF (aHBGF also known as HBFG-1 or FGF-1) and basic HBGF (bHBGF also known as HBGF-2 or FGF-2), are potent mitogens for cells of mesodermal and neuroectodermal lineages, including endothelial cells (see, e.g., Burgess et al., Ann. Rev. Biochem. 58:575–606 (1989)). In addition, HBGF-1 is chemotactic for endothelial cells and astroglial cells. Both HBGF-1 and HBGF-2 bind to heparin, which protects them from proteolytic degradation. The array of biological activities exhibited by the HBGFs suggests that they play an important role in wound healing.

Basic fibroblast growth factor (FGF-2) is a potent stimulator of angiogenesis and the migration and proliferation of fibroblasts (see, for example, Gospodarowicz et al., Mol. Cell. Endocinol. 46:187–204 (1986) and Gospodarowicz et al., Endo. Rev. 8:95–114 (1985)). Acidic fibroblast growth factor (FGF-1) has been shown to be a potent angiogenic factor for endothelial cells (Burgess et al., supra, 1989). Other FGF's may be chemotactic for fibroblasts. Growth factors are, therefore, potentially useful for specifically promoting wound healing and tissue repair.

"HBGF-1," which is also known to those of skill in the art by alternative names, such as endothelial cell growth factor (ECGF) and FGF-1, as used herein, refers to any biologically active form of HBGF-1, including HBGF-1.beta., which is the precursor of HBGF-1.alpha. and other truncated forms, such as FGF. U.S. Pat. No. 4,868,113 to Jaye et al., herein incorporated by reference, sets forth the amino acid sequences of each form of HBGF. HBGF-1 thus includes any biologically active peptide, including precursors, truncated or other modified forms, or mutants thereof that exhibit the biological activities, or a subset thereof, of HBGF-1.

Other growth factors may also be known to those of skill in the art by alternative nomenclature. Accordingly, reference herein to a particular growth factor by one name also includes any other names by which the factor is known to those of skill in the art and also includes any biologically active derivatives or precursors, truncated mutant, or otherwise modified forms thereof.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

I claim:

1. A method for treatment of skin comprising:
   treating a subsurface layer of un-damaged skin with a source of electromagnetic energy sufficient to cause stimulation of collagen biosynthesis without thermal damage to the epidermis, in conjunction with applying a wound healing composition to the skin, thereby achieving improved collagenesis in the skin.

2. The method of claim 1 wherein the treatment is repeated serially with more than one day between any successive treatments.

3. A method for treatment of acne scars in skin, comprising:
   treating contiguous subsurface and surface layers of the skin with a source of electromagnetic energy in order to stimulate collagen biosynthesis in the skin without thermal damage to the epidermis, in conjunction with applying a wound healing promoter composition which enhances a healing response in the skin, thereby improving the appearance of the acne scars.

4. A method for treatment of photodamaged skin, comprising:
   treating the layer of skin with a source of electromagnetic energy which stimulates biosynthesis of collagen without thermal damage to the epidermis, in conjunction with applying a wound healing promoter composition to the skin which enhances a healing response, thereby improving the appearance of the photodamaged skin.

5. A method for treatment of wrinkled skin, comprising:
   treating the layer of wrinkled skin with a source of electromagnetic energy which stimulates biosynthesis of collagen without thermal damage to the epidermis, in conjunction with applying a wound healing promoter composition to the skin which enhances a healing response, thereby improving the appearance of the wrinkled skin.

6. A system for treatment of skin, comprising:
a source of electromagnetic energy which is sufficient to stimulate biosynthesis of collagen in the skin without thermal damage to the epidermis; and
a wound healing promoter composition which enhances a healing response in the skin to accelerate cotlagenesis therein, thereby resulting in improved appearance of skin.

7. A method for treatment of undamaged tissue comprising the following steps:

causing a subdermal stimulation of collagen biosynthesis without thermal damage to the epidermis using a source of electromagnetic energy; and applying a wound healing promoter composition to the tissue, such that collagenesis, repair and healing improvement of tissue is accelerated.

* * * * *